(12) United States Patent
Stone et al.

(10) Patent No.: US 8,317,871 B2
(45) Date of Patent: Nov. 27, 2012

(54) MODULAR HUMERAL HEAD RESURFACING SYSTEM

(75) Inventors: Kevin T. Stone, Winona Lake, IN (US); Nicholas M. Cordaro, Oceanside, CA (US)

(73) Assignee: Biomet Manufacturing Corp., Warsaw, IN (US)

( * ) Notice: Subject to any disclaimer, the term of this patent is extended or adjusted under 35 U.S.C. 154(b) by 917 days.

(21) Appl. No.: 10/930,044

(22) Filed: Aug. 30, 2004

(65) Prior Publication Data

US 2005/0107882 A1 May 19, 2005

Related U.S. Application Data

(63) Continuation-in-part of application No. 10/205,386, filed on Jul. 25, 2002, now Pat. No. 6,783,549.

(60) Provisional application No. 60/308,340, filed on Jul. 27, 2001.

(51) Int. Cl.
*A61F 2/32* (2006.01)
(52) U.S. Cl. .................................................. 623/22.17
(58) Field of Classification Search .... 623/19.11–19.14, 623/18.11
See application file for complete search history.

(56) References Cited

U.S. PATENT DOCUMENTS

| | | | |
|---|---|---|---|
| 4,042,980 A | | 8/1977 | Swanson et al. |
| 4,550,450 A | * | 11/1985 | Kinnett ........................ 623/20.11 |
| 4,662,891 A | * | 5/1987 | Noiles ......................... 623/22.31 |
| 4,731,088 A | * | 3/1988 | Collier ........................ 623/22.13 |
| 4,846,839 A | | 7/1989 | Noiles |
| 4,846,840 A | * | 7/1989 | Leclercq et al. ............ 623/22.15 |
| 4,964,865 A | * | 10/1990 | Burkhead et al. ........... 623/19.11 |
| 5,314,479 A | * | 5/1994 | Rockwood et al. ......... 623/19.14 |
| 5,358,526 A | | 10/1994 | Tornier |
| 5,472,444 A | * | 12/1995 | Huebner et al. ................. 606/64 |
| 5,489,309 A | * | 2/1996 | Lackey et al. .............. 623/19.14 |
| 5,507,818 A | | 4/1996 | McLaughlin |

(Continued)

FOREIGN PATENT DOCUMENTS

EP 1598034 11/2005

(Continued)

OTHER PUBLICATIONS

European Application Partial Search Report EP06254732 mailed Mar. 5, 2009 claiming benefit of U.S. Appl. No. 11/225,645, filed Sep. 13, 2005.

(Continued)

*Primary Examiner* — Thomas J Sweet
*Assistant Examiner* — Ann Schillinger
(74) *Attorney, Agent, or Firm* — Harness, Dickey

(57) ABSTRACT

A two piece humeral component for use in joint arthroplasty which is adapted to be implanted into a joint and engaged by a socket component of the joint. The joint component includes a body having a first articulating surface and a second medial surface opposite the first articulating surface. The first articulating surface is adapted to be engaged by the socket and the second medial surface is adapted to be secured to mounting portion. The mounting portion has a first surface and a second medial surface. The first surface is adapted to be fixably engaged to the second mounting portion of the humeral component. The second medial surface is adapted to be secured to the humerus. A peg which has a first end adapted to engage a cavity found in the humerus is disposed on the mounting portion's second medial surface.

26 Claims, 16 Drawing Sheets

U.S. PATENT DOCUMENTS

| | | | |
|---|---|---|---|
| 5,571,203 A | 11/1996 | Masini | |
| 5,800,551 A * | 9/1998 | Williamson et al. | 623/19.11 |
| 5,928,285 A * | 7/1999 | Bigliani et al. | 623/19.13 |
| 5,976,144 A * | 11/1999 | Fishbein et al. | 606/80 |
| 6,045,581 A * | 4/2000 | Burkinshaw | 623/18.11 |
| 6,146,423 A | 11/2000 | Cohen et al. | |
| 6,197,063 B1 * | 3/2001 | Dews | 623/19.14 |
| 6,228,120 B1 * | 5/2001 | Leonard et al. | 623/19.12 |
| 6,364,910 B1 * | 4/2002 | Shultz et al. | 623/19.13 |
| 6,368,353 B1 * | 4/2002 | Arcand | 623/19.13 |
| 6,494,913 B1 * | 12/2002 | Huebner | 623/19.11 |
| 6,673,114 B2 * | 1/2004 | Hartdegen et al. | 623/19.12 |
| 6,676,705 B1 * | 1/2004 | Wolf | 623/19.14 |
| 6,736,852 B2 * | 5/2004 | Callaway et al. | 623/19.14 |
| 6,783,549 B1 * | 8/2004 | Stone et al. | 623/19.14 |
| 2001/0047210 A1 | 11/2001 | Wolf | |
| 2001/0053935 A1 * | 12/2001 | Hartdegen et al. | 623/19.12 |
| 2002/0016634 A1 * | 2/2002 | Maroney et al. | 623/19.14 |
| 2002/0022889 A1 * | 2/2002 | Chibrac et al. | 623/18.11 |
| 2002/0099445 A1 * | 7/2002 | Maroney et al. | 623/19.14 |
| 2002/0120339 A1 * | 8/2002 | Callaway et al. | 623/19.14 |
| 2003/0028253 A1 | 2/2003 | Stone et al. | |
| 2003/0055507 A1 | 3/2003 | McDevitt et al. | |
| 2003/0100952 A1 | 5/2003 | Rockwood et al. | |
| 2003/0125810 A1 * | 7/2003 | Sullivan et al. | 623/22.17 |
| 2003/0158605 A1 | 8/2003 | Tornier | |
| 2004/0034431 A1 * | 2/2004 | Maroney et al. | 623/19.14 |
| 2005/0004675 A1 | 1/2005 | Shultz et al. | |
| 2005/0107882 A1 | 5/2005 | Stone et al. | |

FOREIGN PATENT DOCUMENTS

| | | |
|---|---|---|
| FR | 2578739 | 9/1986 |
| FR | 2579454 | 10/1986 |
| FR | 2704747 | 11/1994 |
| WO | WO01/67988 | 3/2001 |
| WO | WO02/17822 | 3/2002 |

OTHER PUBLICATIONS

Final Office Action for U.S. Application No. 11/225,645 Mailed Jul. 30, 2009.

Final Office Action for U.S. Application No. 11/225,645 Mailed Sep. 10, 2010.

Non-Final Office Action for U.S. Application No. 11/225,645 Mailed Feb. 5, 2009.

Non-Final Office Action for U.S. Application No. 11/225,645 Mailed Mar. 11, 2010.

O Levy, et al., "Cementless Surface Replacement Arthroplasty of the Shoulder," The Journal of Bone and Joint Surgery, vol. 83-B, No. 23, Mar. 2001, pp. 213-221.

Copeland Shoulder—Report produced by Biomet & Merck.

* cited by examiner

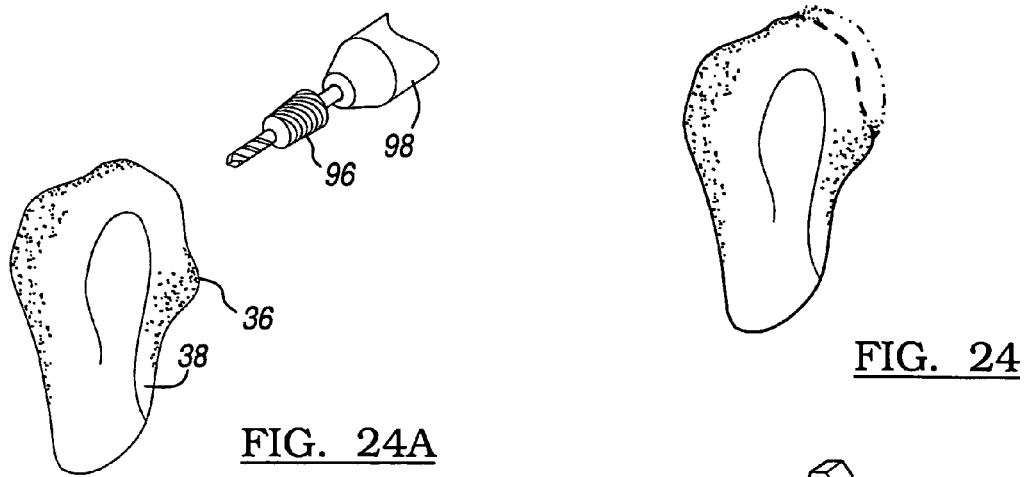
FIG. 24
FIG. 24A
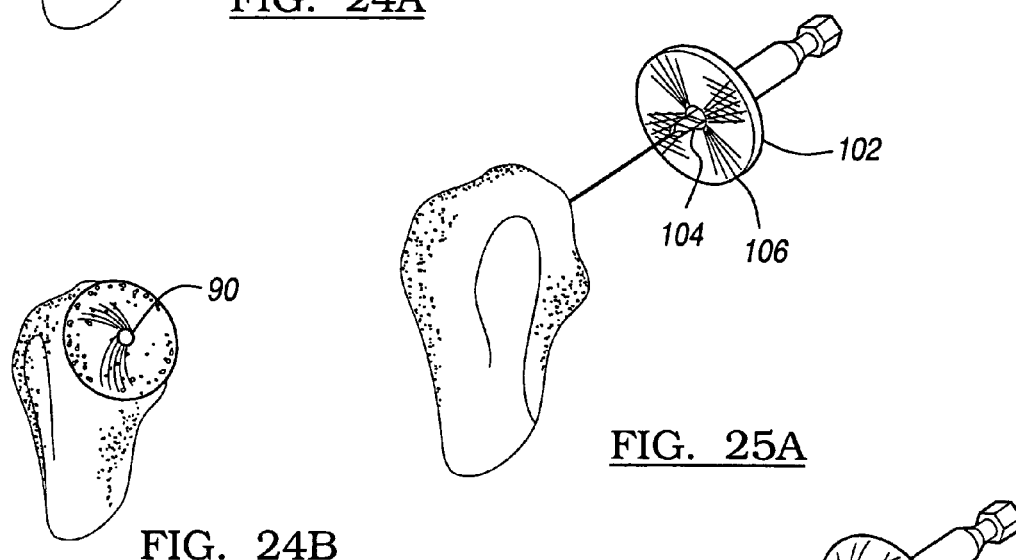
FIG. 25A
FIG. 24B
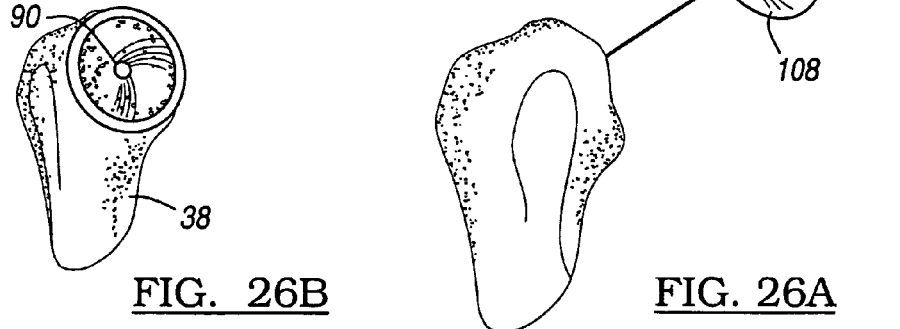
FIG. 26B
FIG. 26A

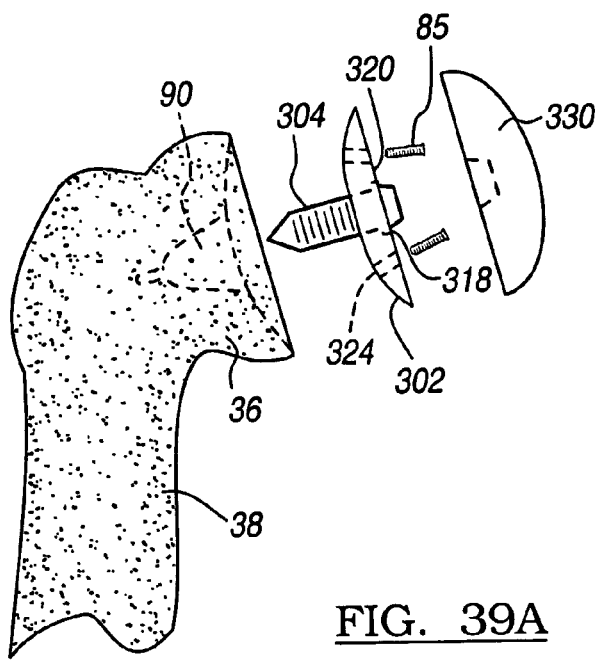
FIG. 39A
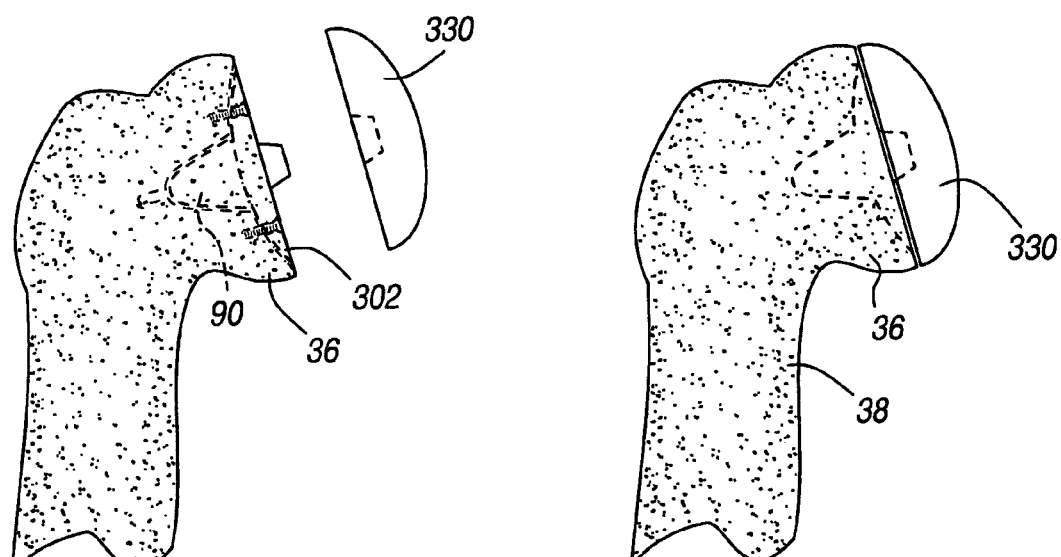
FIG. 39B
FIG. 39C

MODULAR HUMERAL HEAD RESURFACING SYSTEM

CROSS-REFERENCE TO RELATED APPLICATIONS

This application is a continuation-in-part application of U.S. patent application Ser. No. 10/205,386 filed on Jul. 25, 2002, issued as U.S. Pat. No. 6,783,549 on Aug. 31, 2004. This application claims the benefit of U.S. Provisional Application No. 60/308,340, filed on Jul. 27, 2001. The disclosure of the above applications is incorporated herein by reference.

BACKGROUND OF THE INVENTION

1. Field of the Invention

This invention relates generally to an apparatus and method for shoulder arthroplasty and, more particularly, to a humeral component and other associated surgical components and instruments for use in shoulder arthroplasty.

2. Discussion of the Related Art

A natural shoulder joint may undergo degenerative changes due to a variety of etiologies. When these degenerative changes become so far advanced and irreversible, it may ultimately become necessary to replace a natural shoulder joint with a prosthetic shoulder joint. When implantation of such a shoulder joint prosthesis becomes necessary, the natural head portion of the humerus is resected and a cavity is created in the intramedullary canal of the host humerus for accepting a humeral component. The humeral component includes a head portion used to replace the natural head of the humerus. Once the humeral component has been implanted, the humeral cavity positioned at the scapula socket may also be resurfaced and shaped to accept a glenoid component. The humeral component generally includes an articulating surface which engages and articulates with the socket portion of the glenoid component.

It is generally known in the art to provide a shoulder joint prosthesis having a humeral component, as discussed above. However, current prior art humeral components along with the associated surgical components and instruments utilized during shoulder arthroplasty suffer from many disadvantages.

For example, since the humeral component is subject to various types of loading by the glenoid component, the humeral component must offer a stable and secure articulating surface. To achieve this, some humeral components provide a post or stem attached to a lateral surface of the prosthetic humeral head. These humeral components are generally a single piece system with a single stem, which is inserted and cemented into a hole bored deeply into the intramedullary cavity. However, such existing humeral components also exhibit several disadvantages. For example, these types of stemmed humeral components utilize a large stem to stabilize and secure the humeral component to the humerus. Such humeral components increase the amount of bone tissue removed, while also increasing the labor and complexity of the shoulder arthroplasty. Other stemmed humeral components may offer a larger diameter stem. However, the larger diameter stem also requires excess bone tissue to be removed which may not be practical in some patients.

Other prior art humeral components, such as that disclosed in WO 01/67988 A2 sets out a stemless humeral component or head that provides an integral cruciform shape that includes two planar intersecting fins. While this type of humeral component addresses the amount of bone tissue removed, this type of system provides little versatility or adjustments to a surgeon performing the shoulder arthroplasty. Moreover, this type of system does not provide additional enhanced fixation other than the planar intersecting fins.

Additionally, most prior art humeral components only rely on the stem to secure the humeral component into the intramedullary canal, via a cement mantle or bone attachment. The stem may also include grooves or holes, which act as an anchor, once the stem is cemented within the intramedullary canal. The medial surface of most humeral components are thus generally overlooked to enhance cement fixation and are therefore generally smooth. Although some humeral components may include a few longitudinal grooves and others may include both grooves and depressions on the medial surface, such surface enhancements only utilize or texture a portion of the medial surface, thereby not advantageously using the entire medial surface.

What is needed then is a modular humeral component and associated surgical components for use in shoulder arthroplasty which do not suffer from the above-mentioned disadvantages. This in turn, will provide a humeral component which is stable and secure, reduces the overall amount of bone tissue required to be removed, increases a surgeon's available components utilizing a single sized post, reduces the overall surgical time and complexity, increases overall medial surface area, enhances and increases post strength without increasing overall post diameter, provides a fully enhanced or textured medial surface for enhanced cement fixation or bone fixation and increased overall stability, provides for a uniform cement mantle, and provides increased tensile and shear strength. It is, therefore, an object of the present invention to provide such a humeral component and associated surgical components for use in shoulder arthroplasty.

SUMMARY OF THE INVENTION

In accordance with the teachings of the present invention, an apparatus and method for shoulder arthroplasty is disclosed. The apparatus and method employs a modular humeral component and other associated surgical components for use in the shoulder arthroplasty. In this regard, the modular humeral component is adapted to be implanted into a humerus and engaged by a glenoid portion of a scapular component.

In one preferred embodiment, a modular humeral component is used for shoulder arthroplasty such that the humeral component is adapted to be implanted into a humerus and engage a glenoid component. The humeral component includes a head member having a first articulating surface and a second fixation surface, which is opposite to the first articulating surface. The first articulating surface is adapted to engage the articulating surface of the glenoid component and the second fixation surface is adapted to engage a fixation component. The fixation component has a first surface adapted to be secured to the head member and a second surface that is generally opposite the first surface. The second surface includes a fixation member adapted to be secured to the humerus.

Use of the present invention provides an apparatus and method for shoulder arthroplasty, and specifically, a modular humeral component and associated surgical components for use in shoulder arthroplasty. As a result, the aforementioned disadvantages associated with the currently available humeral components and associated surgical components for shoulder arthroplasty have been substantially reduced or eliminated.

BRIEF DESCRIPTION OF THE DRAWINGS

Still other advantages of the present invention will become apparent to those skilled in the art after reading the following specification and by reference to the drawings in which:

FIGS. 24-26b illustrate a method for preparing the humerus implantation of the humeral component using associated surgical components according to the teachings of the preferred embodiment of the present invention;

FIG. 39a-39c represents the intention of a fixation member.

DETAILED DESCRIPTION OF THE PREFERRED EMBODIMENTS

The following description of the preferred embodiments concerning an apparatus and method for shoulder arthroplasty is merely exemplary in nature and is in no way intended to limit the invention, its application, or uses.

Figure 1:
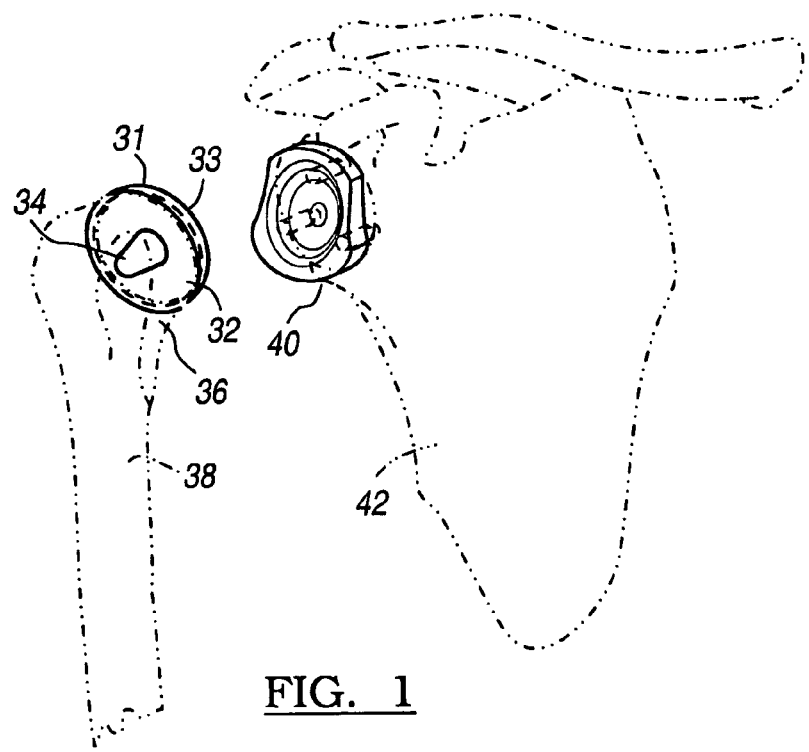
FIG. 1 is a perspective view of the humeral component according to the teachings of the preferred embodiment of the invention shown implanted in a skeletal structure.

FIG. 1 depicts the components used in the shoulder arthroplasty of the current invention. As shown, the modular humeral component 31 has a base member 32 and a head member 33. The base member 32 has a fixation peg 34, which is used to attach the humeral component to the resected portion 36 of the humerus 38. If a total shoulder arthroplasty is performed, a glenoid component 40 is first implanted into the scapula 42 using techniques well known in the art. The glenoid component 40 is preferably of the type disclosed in U.S. Pat. No. 5,800,551, which is hereby incorporated by reference, or other suitable conventional glenoid components. The humeral component 31 is designed to allow rotational and transitional movement of the head member 33 with respect to the glenoid component 40.

Figure 2A:
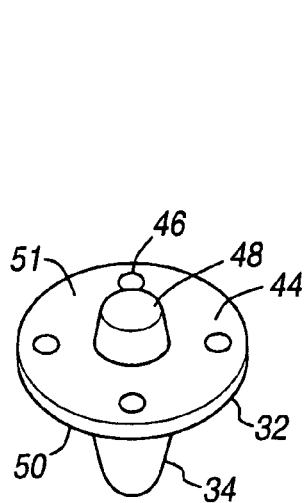
FIGS. 2a-2c are views of the fixation member of humeral component of FIG. 1.
Figure 2B:
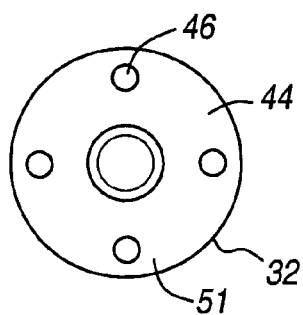
Figure 2C:
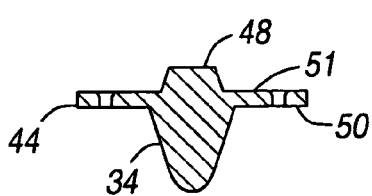
Figure 3A:
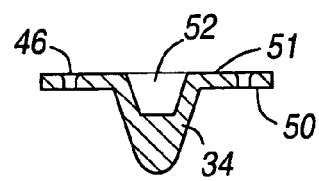
FIGS. 3a-9 are alternate embodiments for the fixation member of the humeral component of the present invention.

FIGS. 2a-2c depict the base member 32 of one embodiment of the current invention. The base member 32 is defined by a shelf member 44, which may have a plurality of through holes 46. The shelf member 44 can have at least one mating member 48 for engaging the head member 33 of the humeral component 31. It is preferred that the mating member 48 be a defined Morse taper or other suitable attaching mechanism. In addition to the mating member 48, each base member 32 has a fixation peg 34 disposed on the lower lateral surface 50 of shelf member 44. The fixation peg 34 is generally perpendicular to the shelf member for its entire length of the fixation peg 34. As depicted in FIGS. 2a-3, the shelf member 44 of the base member 32 can define flat lower lateral surface 50 and flat generally parallel upper surfaces 51. FIG. 3a shows the second embodiment of the current invention, which has a cavity 52 defined in the shelf member 44. The cavity 52 is preferably the female side of a Morse taper, which would engage a male Morse taper on the head member 33.

Figure 3B:
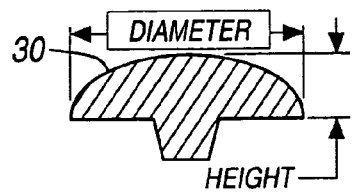

FIG. 3b shows the head member 33 which mates with the base member 32 of FIG. 3a. It should be noted that a surgical kit of the components would contain numerous head members 33, each having a varied radius of curvature, diameter, and height to allow a surgeon to optimize joint movement. Additionally, a surgical kit would contain the instruments needed for implantation (shown later).

The head member 33 and base member 32 must be made of bio-compatible materials such as, without limitation, titanium, titanium alloys, surgical alloys, stainless steels, biocompatible ceramics, and cobalt alloys. Optionally, the base member 32 can additionally be made of materials such as biocompatible ceramics and resorbable and non-resorbable polymers and other anticipated bio-compatible metallic or polymeric materials. Should the base member 32 be made of non-metallic components, a fastener would be needed to couple the head 33 to the base 32.

Figure 4:
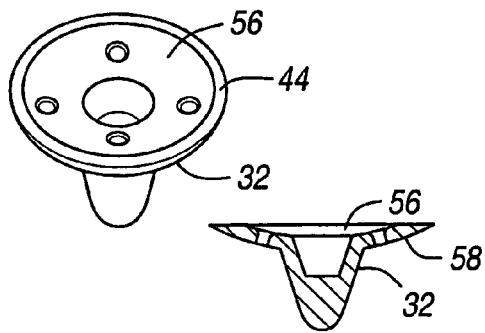
Figure 5:
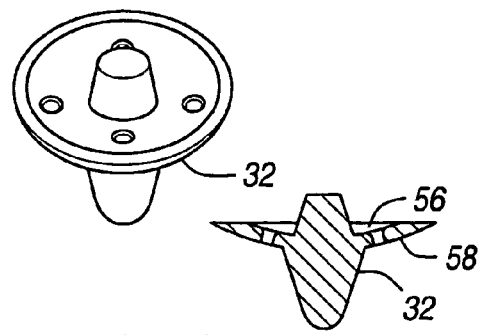

As shown in FIGS. 4-7, the shelf members 44 need not to be planar. FIGS. 4 and 5 show the base member 32 and having an interior concave surface 56 and a convex medial surface 58. Base members, as disclosed in FIGS. 4 and 5 would be used in situations where maximum bone removal in the humerus 38 is required. In each situation, the head member 33 would have a convex medial surface 59 for engaging the concave surface 56. It is envisioned as with all of the embodiments that the base members 32 and head member 33 can be coupled using the mating member 48, i.e., Morse taper. The use of the convex-concave interface provides a coupling interface which is self centering under a multitude of loading conditions. The interface reduces the occurrence of micro-motions which can disrupt the normal functioning of the joint prosthesis as well as lead to premature component failures. Any loads applied to the articulating surface of the head member 33, are transferred as a perpendicular force into the base member 32 of the modular humeral component 31 through the non-planar shelf member 44.

Figure 6:
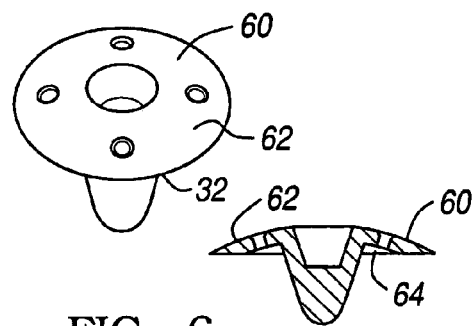
Figure 7:
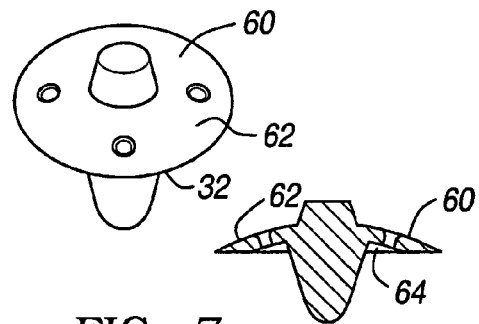

FIGS. 6 and 7 define base members 32 having the shelf member 60 having a convex outer surface 62. Additionally shown is a concave inner surface 64 for mating with a resected head 36 of the humerus 38. The base members as depicted in FIGS. 6 and 7 can be used when minimal bone removal is possible and will generally encapsulate the hemispheric shape cut into the humerus 38 as described later. As with the base members as shown in FIGS. 4 and 5, any loads applied to the articulating surface of the head member 33, are transferred as a perpendicular force into the base member 32 of the modular humeral component 31.

Figure 8:
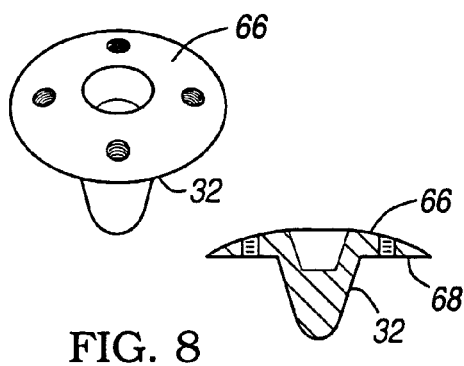
Figure 9:
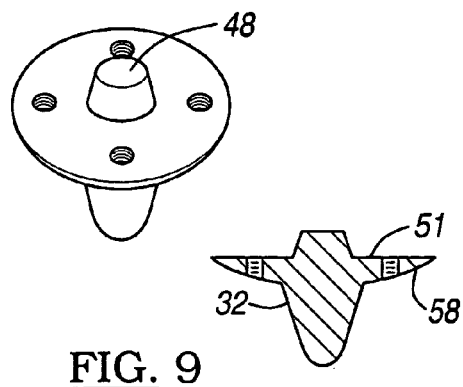

FIGS. 8 and 9 disclose alternate embodiments of the base member 32 for the humeral component 31. FIG. 8 depicts the base member 32 having a convex outer surface 66 and a flat lateral surface 68. The base members as depicted in FIGS. 2a-3 and 8 can be utilized when a moderate amount of bone material must be removed from the resected head 36 of the humerus 38. FIG. 9 depicts the base member 32 having a flat upper surface 51 and a convex lateral surface 58. This base member would readily utilize the head member 33 as used with the base member as depicted in FIG. 2a. It is envisioned that either base member can have a defined male or female mating member 48 in the form of a Morse taper.

Figure 10:
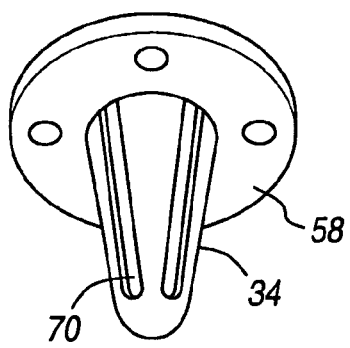
FIGS. 10-12 represent alternate peg configurations for the fixation member of the humeral component of the present invention.
Figure 11:
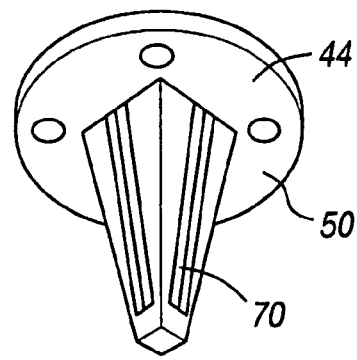
Figure 12:
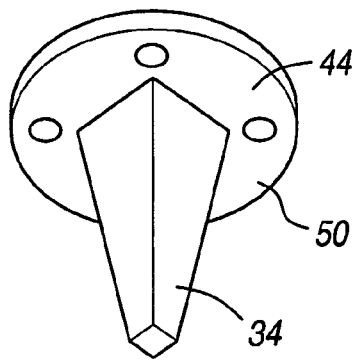

FIGS. 10-12 depict possible configurations for the fixation peg 34. FIG. 10 shows the fixation peg 34 defining a plurality of flutes 70 therein. As can be seen, the modular system does not need a shelf member 44. Without the shelf member 44, the base can have either a male or female Morse taper. FIGS. 11 and 12 depict the fixation peg 34 being at a tapered prism with the base of the prism coupled to the lower lateral surface 50 of the shelf member 44.

Figure 13:
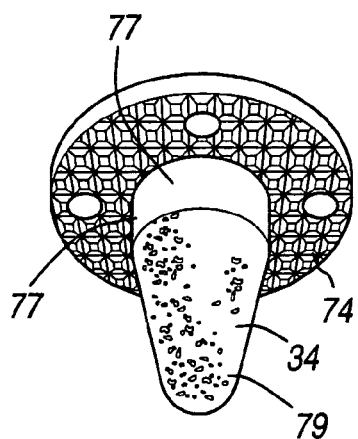
FIGS. 13 and 14 represent alternate texturing, which is usable in the humeral components of the present invention.
Figure 14:
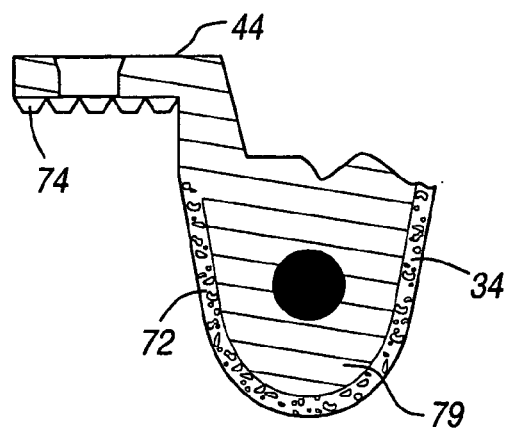

FIGS. 13 and 14 depict possible surface treatments for the lower lateral surface 50 of the shelf member 44 and fixation peg 34. All of the possible fixation pegs 34 can have a porous coated region 72, which will assist in the fixation of the component to the humerus 38. Additionally, all of the lower lateral surfaces 50 of the shelf member 44 can define a waffle pattern 74 to assist in the incorporation of bone cement. Each fixation peg 34 extends from the lower lateral surface 50 to define or fill in a coupling region 75 having a diameter of about 0.50 inches. Each coupling region 75 also includes a sidewall 77 formed with and from the lower lateral surface 50. The coupling region 75 provides a smooth flat surface for which the fixation peg 34 extends out, and reduces or eliminates any stress risers about each fixation peg 34, which could be caused by positioning the lower lateral surface 50 immediately adjacent the fixation peg 34.

The fixation peg 34 includes a first end 79, which is inserted into or engages a cavity or hole formed within a cavity in the humerus and a second end 81, which extends from or is integral with the shelf member 44. The first end 79 is semi-spherical and the second end has a 0.25 inch radius about the circumference of the second end 81 of the peg, which blends into a flat or smooth portion of the coupling region 75 to decrease the overall sheer stress of the fixation peg 34. Optionally, should the fixation peg be non-metallic, embedded within the first end of each fixation peg 34 is a tantalum ball 83. The tantalum ball 83 enables the humeral component 31 to be easily identified in an x-ray.

Figure 15:
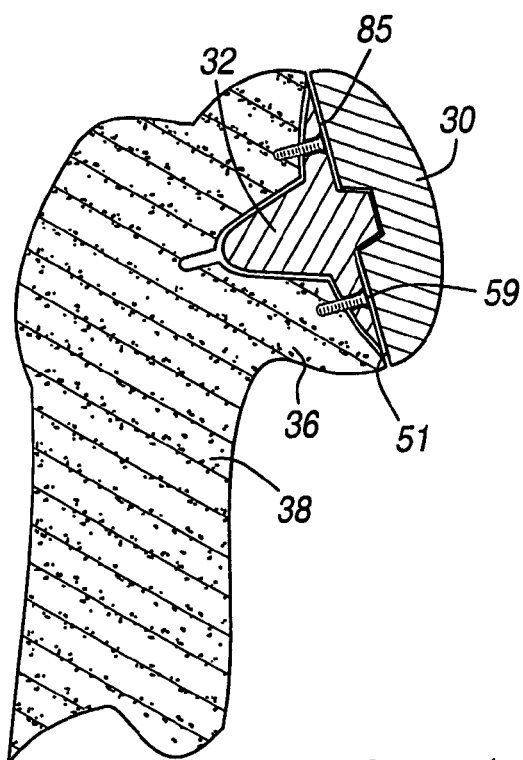
FIGS. 15 and 16 represent cross-sectional views of implanted humeral components of the present invention.
Figure 16:
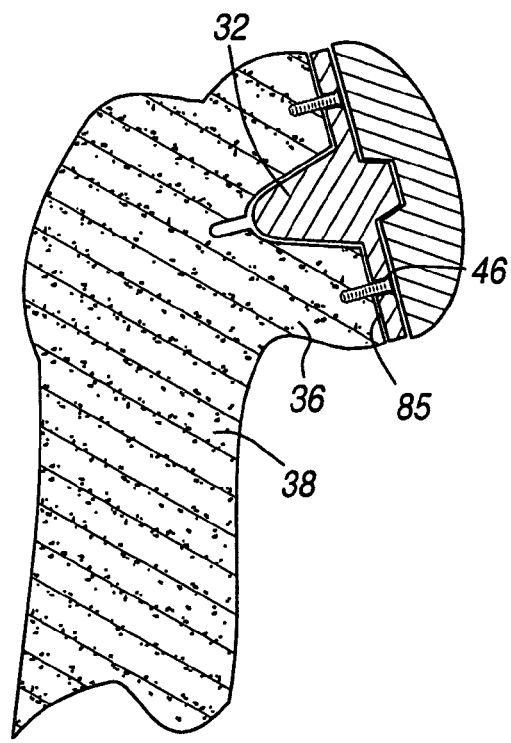

FIGS. 15 and 16 depict cross-sectional views of various embodiments of the current invention implanted into resected head 36 of humerus 38. As depicted in FIG. 16, when a large amount of bone mass must be removed during the arthroplasty, the base member 32 as depicted in FIG. 9 can be used. As is shown, the base member 32 is fixed to the humerus 38 using a plurality of screws 85. The lateral surface 59 of the head member 33 defines a cavity 52 for receiving the mating member 48 or Morse taper post.

As with the base member depicted in FIG. 15, the base member 32 is held to the humerus 38 by use of screws 85 disposed through the holes 46. FIG. 16 discloses the use of the base member 32 as depicted in FIG. 3a which is similarly held in place by use of fixation screws 85 to the humerus 38.

Figure 17:
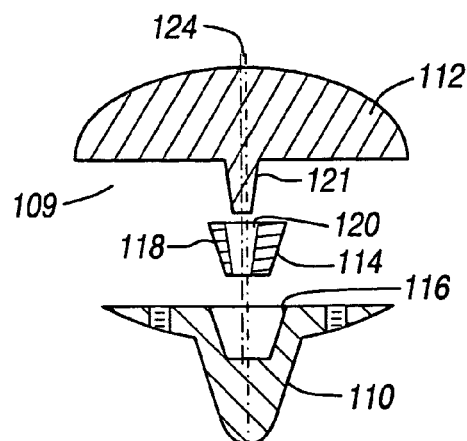
FIGS. 17 through 22 depict an alternate embodiment of the present invention having an insert member disposed between the head and the base member.
Figure 18:
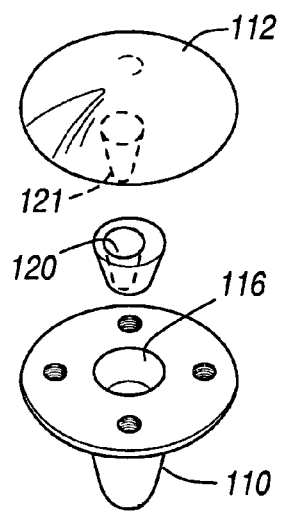

FIGS. 17 through 18 show an alternate embodiment of the humeral component 109. Base member 110 is shown having a modified Morse taper cavity 116. The humeral component 109 further has a head portion 112 with a male Morse taper portion 121. Disposed between the head portion 112 and the base member 110 is a coupling member 114. Coupling member 114 has an outer surface 118 which acts as the male portion of a Morse taper to bond with the cavity 116 of the base member 110. Coupling member 114 further defines a female portion 120 of a Morse taper which corresponds to the male portion 121 of the Morse taper of the head portion 112. The coupling portion 114 functions to move the center of curvature of the head portion 112 a fixed distance 123 from the center line of the base member 110. This functions to effectively change the centering location of the head portion 112 with respect to the humerus 138, thus allowing the surgeon more flexibility.

Figure 19:
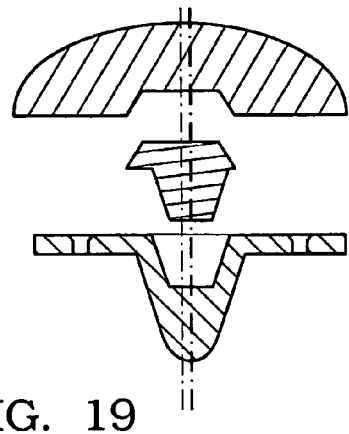
Figure 17A:
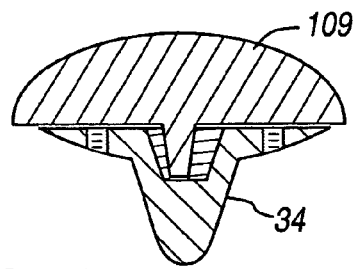
Figure 19A:
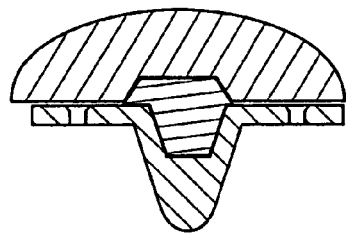
Figure 19B:
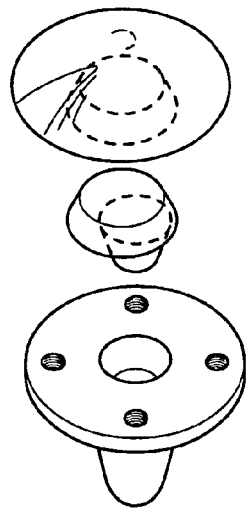

FIG. 17a shows the alternate humeral component 109 in its assembled configuration. FIG. 18 shows an exploded view of the alternate humeral component 109, coupling member 114, and base member 110. Rotation of coupling member 114 allows for translation of the head portion 112 on the base member 110. FIGS. 19 through 19b depict a head portion 112 having a female Morse taper cavity 116 which engages a male Morse taper 115 on alternate coupling member 114. FIG. 19a depicts an assembled view of the alternate humeral component 109.

Figure 21A:
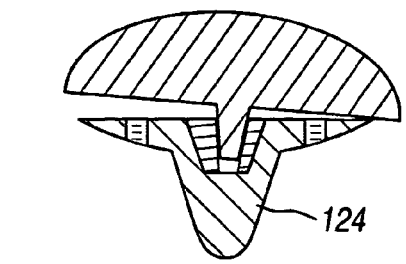
Figure 21:
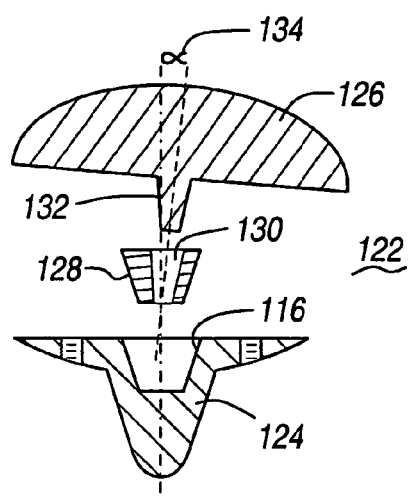
Figure 21B:
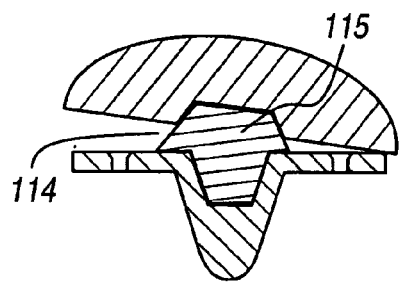

FIGS. 21 through 21b depict an alternate embodiment of the humeral component 122. Shown is the base member 124 which has a modified female cavity defining a Morse taper 116. The head portion 126 has a coupling male Morse taper 132 disposed on the medial surface of the head component 126. Disposed between the head portion 126 and the base portion 124 is the coupling member 128. The coupling member 128 defines an outer surface 118 which functions as the male portion of the Morse taper and couples to the female portion 116 of the base member 124. The coupling member 128 further defines an interior cavity 130 which functions as a female Morse taper for the male Morse taper 132 of the head 126. The interior cavity 130 of the coupling member has an offset angle 134, which functions to rotate the center of curvature of the head portion 126 with respect to the base member 124. Similarly, shown in FIG. 21b is a coupling member 114 having a male Morse taper 115 being angled.

Figure 20:
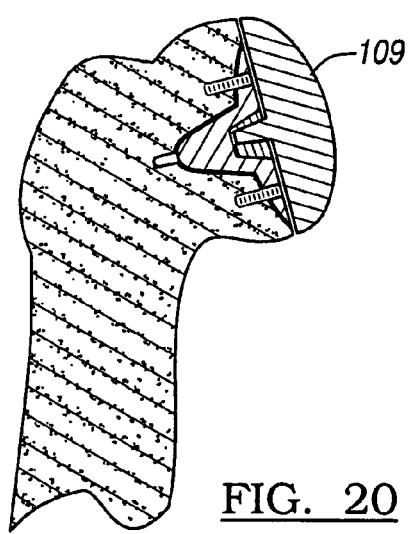
Figure 22:
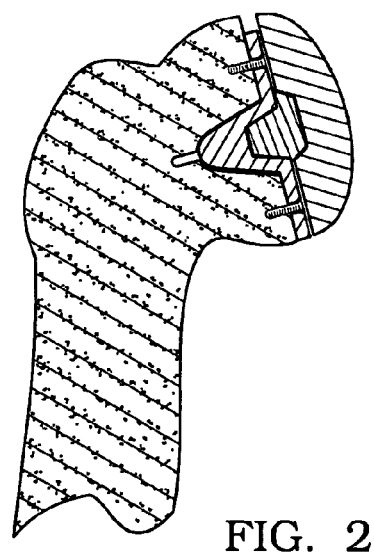

FIGS. 20 and 22 show the alternate humeral components 122 inserted into a resected humerus. As with the other humeral components, the base member is fixed to the head of the humerus using fasteners.

FIGS. 23a-23e depict another alternate embodiment of the present invention. Shown is a shelfless base member 232 which is formed by a fixation peg 234. Each fixation peg 234 has three evenly spaced triangular fins 236 disposed thereon. The triangular fins 236 have an edge 239 which is co-planar to a top surface 238 of fixation peg 234. Incorporated into a top surface 238 of the fixation peg 234 is a fixing mechanism 240.

Figure 23B:
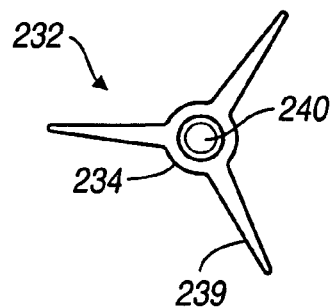
FIGS. 23a-23e depict another alternate embodiment of the present invention having flanges disposed on a shelfless base member.
Figure 23A:
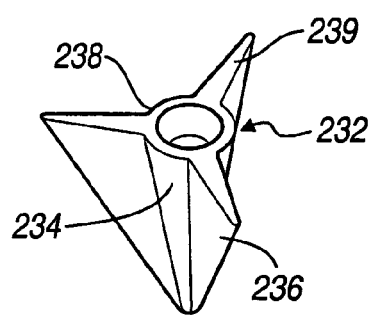
Figure 23C:
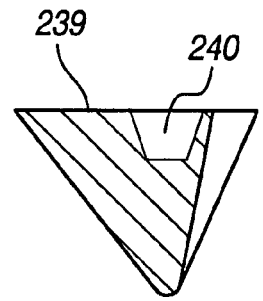
Figure 23D:
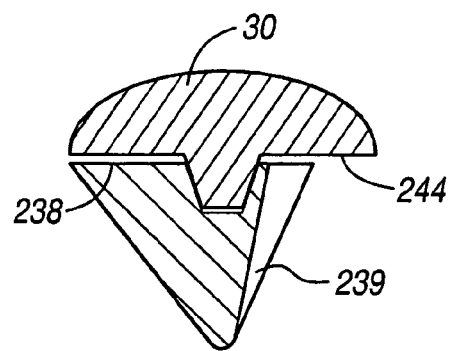
Figure 23E:
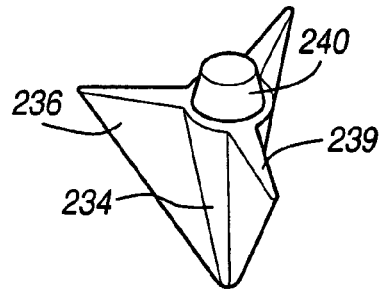

FIGS. 23a and 23b disclose fixing mechanism 240 in the form of a female Morse taper as the fixation which functions to couple the head 30 onto the base member 232 (see FIG. 23d). As can be seen FIG. 23e, the top surface 238 alternately can have a fixing mechanism 240 in the form of a male Morse taper disposed thereon. It is envisioned that a head member 30 being used in this embodiment can have a lower surface 244 which has a porous coat, plasma spray, grit blast, or smooth surface to facilitate the coupling to the bone.

When the base member 240 is coupled to head member 30, there is a defined gap-between the lower surface 244 of the head 30 and the upper surface 238 of the base member 232. After implantation, the lower surface 244 of head member 30 rests upon the resected bone, not the top surface 238 of the base member 232.

The method for implanting the humeral component 31, along with associate surgical components utilized will now be described with reference to FIGS. 24a-28. The head of the humerus 38 is resected using a saw, chisel then planed flat or with a concavity. With the resected head 36 of the humerus 38 exposed, an alignment or guide hole 90 is first drilled substantially through the center of resected head 36 of the humerus 38 using a quick release drill bit 96 and driver 98. Optionally, the resected head 36 of humerus 38 can be resected to provide a flat surface during the drilling of pilot hole 90.

Once the guide hole 90 is drilled, the resected head 36 of humerus 38 is optionally reamed using a concave spherical reamer shaft 102 with the driver 98. The concave reamer 102 includes a guide pin 104 and a roughened spherical surface 106 substantially corresponding to the spherical shape of the lower medial surface of the shelf member 44 of base member 32. An optional convex reamer surface 108 permits rasping or drilling of tight humeral cavities (see FIGS. 26a and 26b). Upon rotating the surface of the reamer, the bone of the resected head 36 of the humerus 38 is prepared to mate or conform with the shape of the lower lateral surface 50 of the shelf member 44 of the base member 32. As depicted in FIGS. 25a and 26b, the reamer 102 can have a convex shape or alternatively a flat shape, which reams a concave shape into the resected head 36 of the humerus 38. Determining which reamer is used is a function of the preoperative degenerative changes in the humerus 38.

Figure 27:
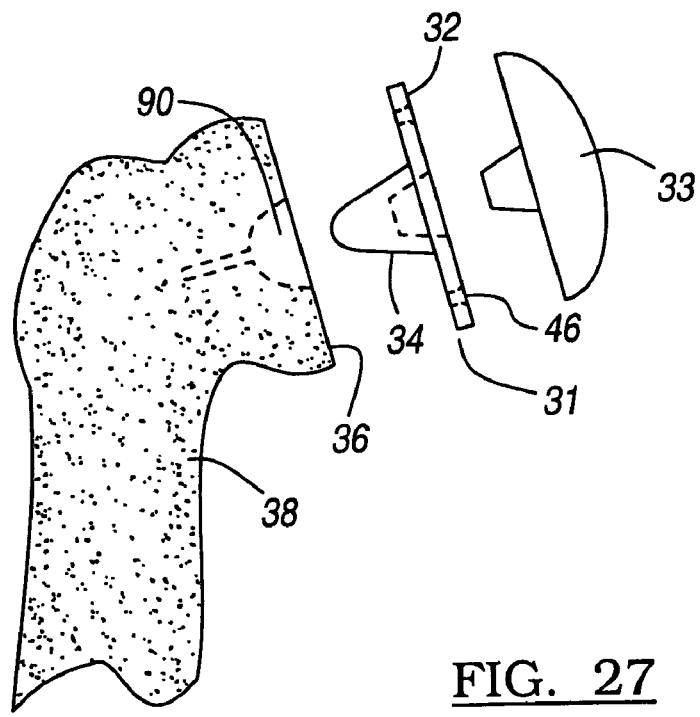
FIGS. 27-28 further illustrate methods for implanting the humeral components into the prepared humerus according to the teachings of the preferred embodiment of the present invention.
Figure 28:
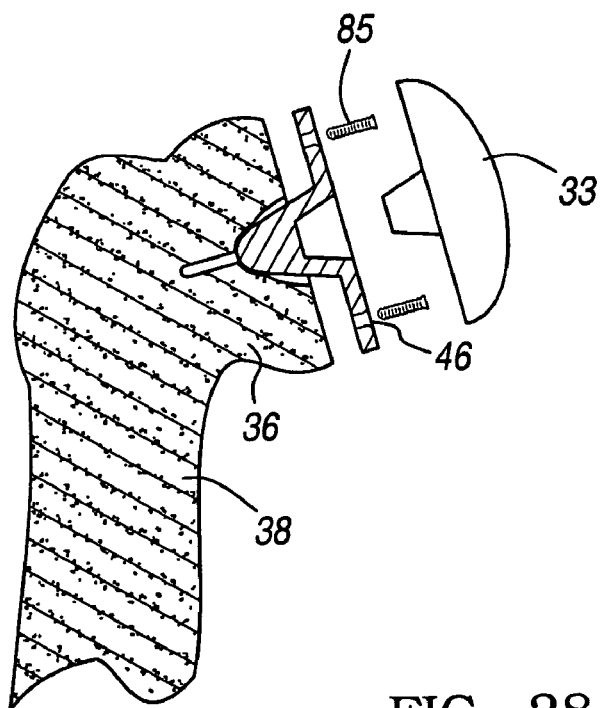

With reference to FIGS. 27-28, which depict the insertion of the humeral components 30, once the surface of the resected head 36 of the humerus 38 has been resected, the base member 32 is inserted into the guide hole 90. It is envisioned that fixation peg 34 of the base member 32 can be forced into the guide hole 90 to displace the bone material around the intramedullary canal. Optionally, the guide hole 90 can also be reamed to a larger interior diameter to accept the base member 32 without displacement of the bone material by the fixation peg 34.

Once the base member 32 has been inserted into the guide hole 90, the optional screws 85 are disposed through the holes 46 to couple the base member 32 to the humerus 38. At this point, a surgeon may use any number of test head portions and/or adapter portions to determine the proper size needed to mate with the glenoid component. Once a proper head member 33 size has been determined, the final head member 33 can be fixed to the shelf member 44 of the base member 32.

FIGS. 26 and 27 show the use of the base member 32 as depicted in FIG. 3. As can be seen, the base member of FIG. 3 is utilized when a minimal amount of bone is required to be removed.

Figure 29A:
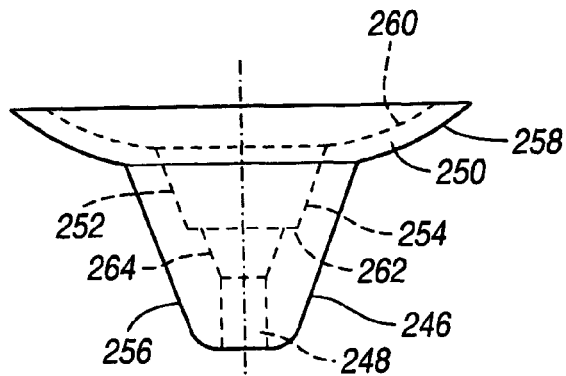
FIGS. 29a-c represent side and perspective views of an alternate fixation member having a through stem fixation bore.
Figure 29B:
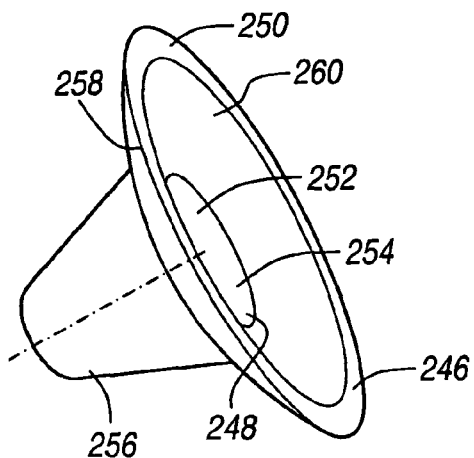
Figure 29C:
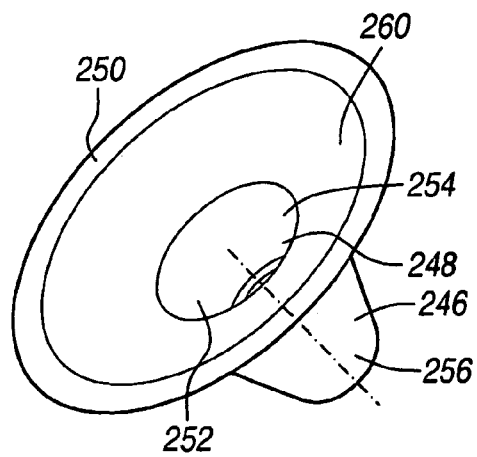

FIGS. 29a-c represent side and perspective views of an alternate fixation member 246 defining a through member fixation bore 248. The shelf member 250 can have at least one mating member 252 for engaging the head member of the humeral component. The mating member 252 can be a defined female Morse taper 254 or other suitable attaching mechanism. In addition to the mating member 252, each fixation member 246 has a fixation peg 256 disposed on the lower lateral surface 258 of shelf member 250. The fixation peg 256 may be perpendicular to the shelf member for the entire length of the fixation peg 256. As depicted in FIGS. 29a-c, the shelf member 250 of the fixation member 246 can define a convex spherical lower lateral surface 258 and concave spherical upper lateral surface 260. FIG. 29a shows hidden lines representing the through member fixation bore 248 formed along a central axis of the fixation member 246. As shown, the female Morse taper 254 is optionally co-linear or concentric with both the through member fixation bore 248 and the fixation peg 256. Adjacent to the bottom 262 of the female Morse taper is a defined conical portion 264 which is configured to accept a head of a bone coupling screw.

Figure 30A:
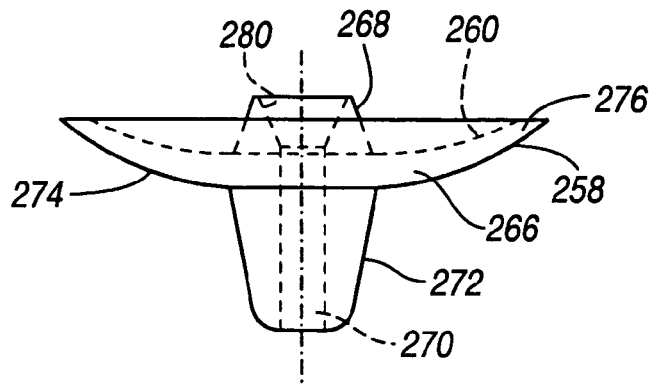
FIGS. 30a-c represent side and perspective views of an alternate fixation member having a male Morse taper with through stem fixation bore.
Figure 30B:
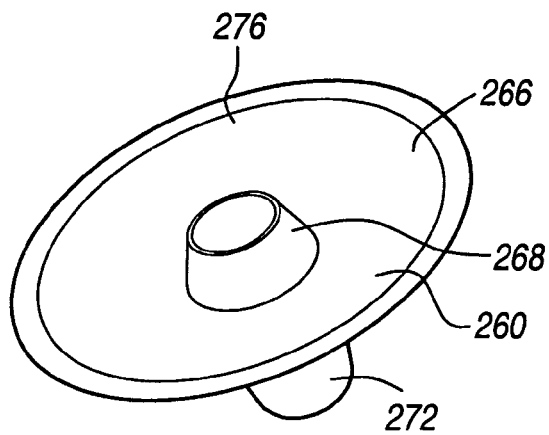
Figure 30C:
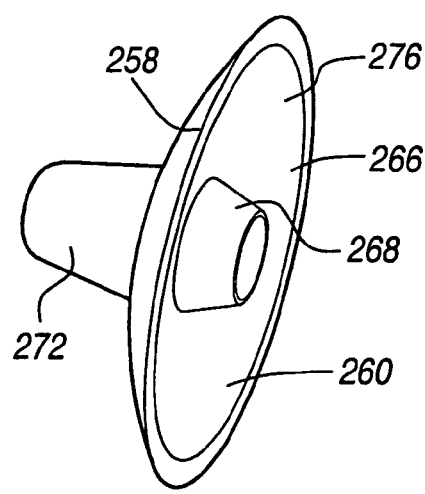

FIGS. 30a-c represent side and perspective views of an alternate fixation member 266 having a mating member 268 in the form of a male Morse taper with a through stem fixation bore 270 for engaging the head member of the humeral component. In addition to the mating member 268, the fixation member 266 has a fixation peg 272 disposed on the lower lateral surface 274 of shelf member 276. The shelf member 276 can define convex spherical lower lateral surface 258 and concave spherical upper lateral surface 260. FIG. 30a shows hidden lines representing the through member fixation bore 270 formed along a central axis of the fixation member 266. As shown, the mating member 268, in the form of a Morse taper, is optionally co-linear with both the through member fixation bore 270 and the fixation peg 272. Disposed through the top 278 of the fixation member 268 is a defined conical portion 280 which is configured to accept a tapered head of a bone coupling screw.

Figure 31A:
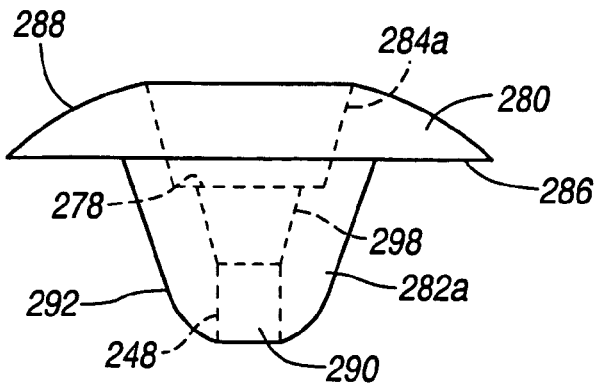
FIGS. 31a-c represent side and perspective views of an alternate fixation member having a female Morse taper with through stem fixation bore.
Figure 31B:
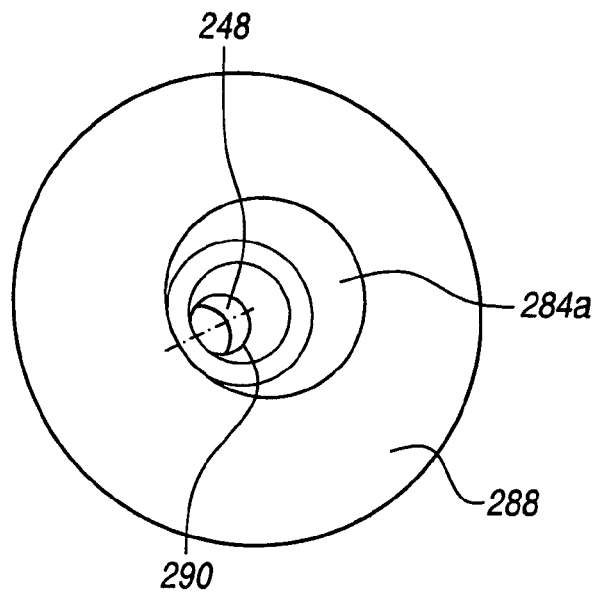
Figure 31C:
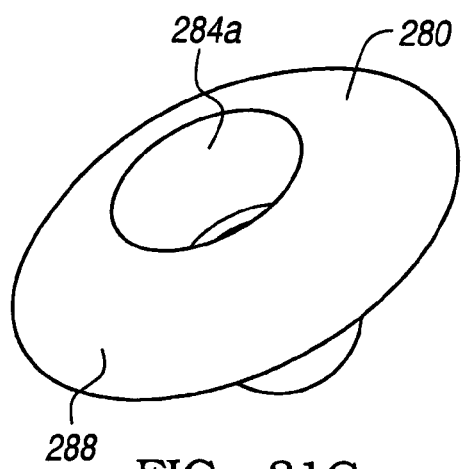
Figure 32A:
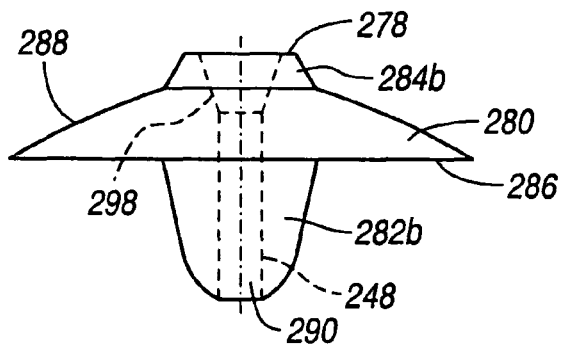
FIGS. 32a-c represent side and perspective views of an alternate fixation member
Figure 32B:
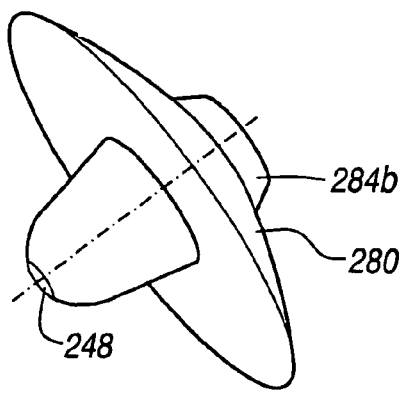
Figure 32C:
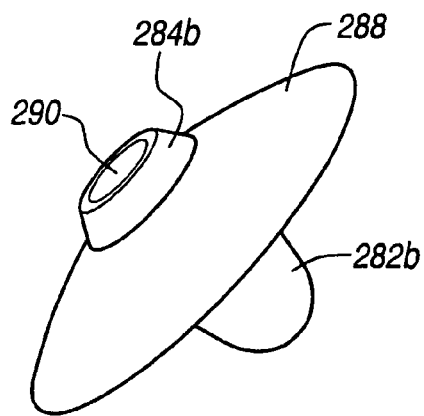

FIGS. 31a-c and 32a-c represent side and perspective views of an alternate fixation members 282a and 282b. The members 282a and 282b have a shelf member 280 with mating features 284a and 284b for engaging the head member of the humeral component. The shelf member 280 of the fixation members 282a and 282b define a flat lower lateral surface 286 and convex spherical upper lateral surface 288. FIGS. 31a and 32a show hidden lines representing the through member fixation bore 290 formed along a central axis of each of the fixation members 282a and 282b. The mating features 284a and 284b in the form of a Morse tapers are optionally co-linear with both the through member fixation bore 290 and a fixation peg 292. Disposed through the top 278 of the mating features 284a and 248b and fully though the fixation members 282a and 282b is a defined fixation bore 248 having a conical screw head supporting portion 298 which is configured to accept a tapered head of a bone coupling screw. This bone coupling screw can be positioned into or extended through the resected bone.

The fixation members depicted in FIGS. 29a through 32c are generally implanted as described above. Generally, a portion of the head of the joint is resected using a rasp or other appropriate cutting tool. A bore is then formed in the resected head. The fixation member is then fixed to the prepared surface. A fastener such as a bone screw then disposed through the fixation bore 290 to fasten the fixation member to the resected bone. At this point, a articulating head (shown in FIG. 1 or 15 through 22) is coupled to the fixation member. While specific fixation members are show in FIGS. 29-32c, the through bore feature is equally applicable to the fixation members shown in FIG. 1-14.

The modular nature of the humeral component 31 of the present invention allow a set of various types of both replacement base members 32 and head members 33 to be formed. In using such a set, a surgeon can interoperably choose the appropriate base member depending on the patient's particular degenerative condition. Additionally, the surgeon can then choose from a set of head members 33, which both have the proper articulating surface radius and a proper coupling to the base member 32.

Figure 33:
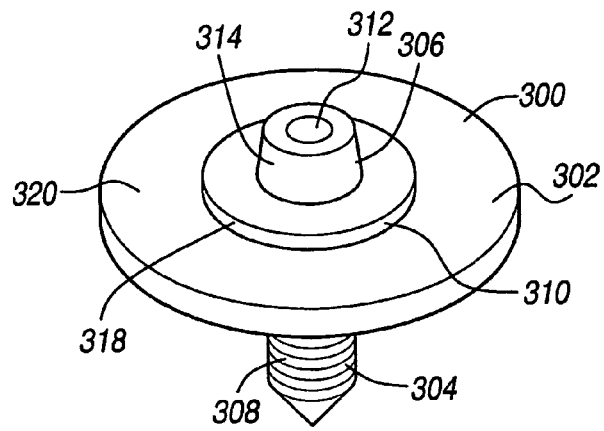
FIG. 33 represents a perspective view of an alternate fixation member.
Figure 34:
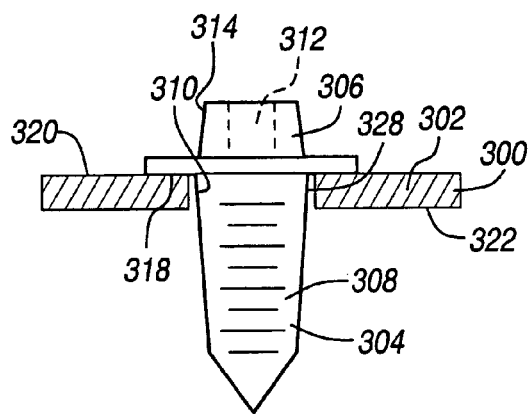
FIG. 34 represents a cross-sectional view of the fixation member shown in FIG. 33.

FIGS. 33 and 34 represents a perspective and cross sectional views of an alternate fixation member 300. The fixation member 300 is formed of two components, a generally circular shelf member 302, and a bone engaging member 304. As described below, after an articulating surface is resected, an appropriate shelf member 302 is positioned against the resected surface. The bone engagement member 304 is then coupled to and through the shelf member 302 into the resected bone. An articulating head (not shown) is coupled to the bone fixation member to form a prosthetic with an articulating surface.

The bone engaging member 304 has a head engagement portion 306 and a threaded bone engagement portion 308. The bone engagement member 304 additionally has a shelf member engagement region 310 and drive feature 312. The shelf engagement region 310 functions to distribute and translate forces from the articulating head into the resected bone. It is envisioned that the shelf engagement region 310 can be an annular engagement flange 318 or textured cylindrical interface surface. The drive feature 312 can be an aperture having at least one defined flat drive surface, such as a hex aperture. The head engagement portion 306 can be a defined male 314 or female 316 Morse taper.

The shelf member 302 can be generally flat or curved. As described in previous embodiments, the shelf member 302 has upper and lower surfaces 320 and 322 which can be flat, concave or convex. The shelf members can additionally define a plurality of through apertures 324 that are configured to accept bone engaging screws to prevent rotation of the shelf member 302 during the insertion of the bone engaging member.

FIG. 34 shows the annular engagement flange 318 is positioned an upper surface 320 of the annular shelf member 302. The shelf member 302 defines an aperture which annularly supports the bone engaging member 304. It is envisioned that the male Morse taper 316 can be used to couple the fixation member to an articulating head (see FIGS. 15-21).

Figure 35:
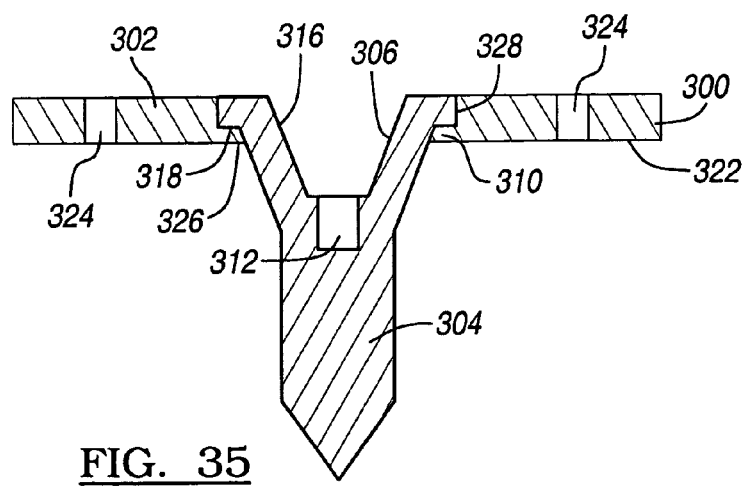
FIG. 35 represents a cross-sectional view of an alternate fixation member.

FIG. 35 represents a cross-sectional view of an alternate fixation member 302. Shown is the bone engaging member 304 having a head engagement portion 306 which is generally located below the shelf member 302. The head engagement portion 306 is shown as a female Morse taper 316. The annular engagement flange 318 is disposed within an annular coupling groove 326 which is formed about the aperture 328 of the shelf member 302. Defined in the bottom of the Female Morse taper 316 is the drive mechanism 312. It is envisioned that the annular coupling groove 326 can take the form of a tapered countersink.

Figure 36B:
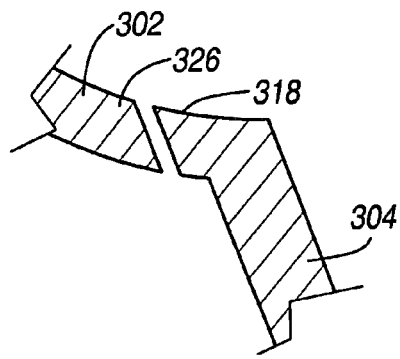
FIGS. 36a and 36b represent an alternate fixation component having a fixation member.
Figure 36A:
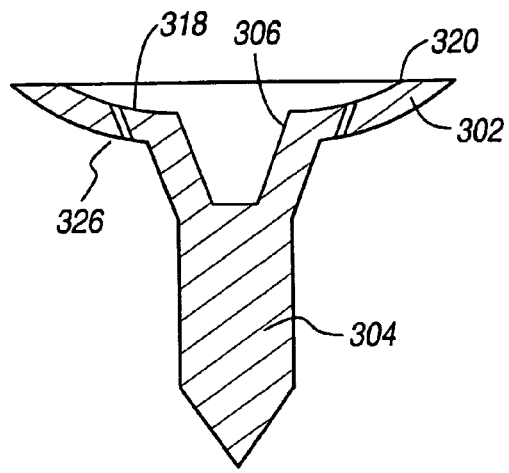

FIGS. 36a and 36b represent an alternate fixation component having a bone fixation member 304. The upper surface 320 of the shelf member 302 is show being concave as previously described. The shelf member has a annular coupling groove 326 which mates with the annular flange 318 of the bone engaging member 304.

Figure 37:
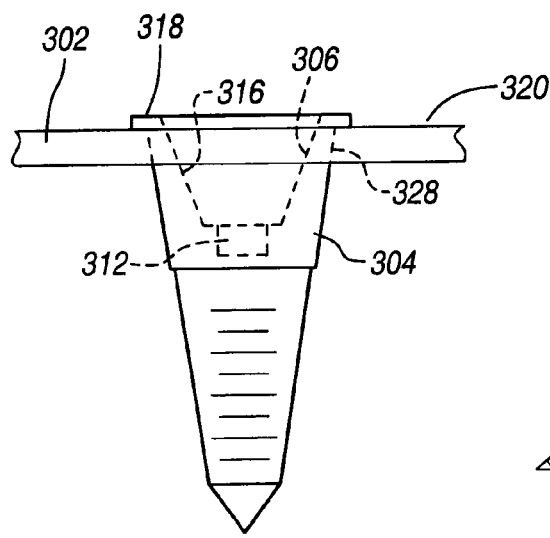
FIG. 37 represents the coupling of a bone engagement member to a fixation shelf.

FIG. 37 represents a cross-sectional view of an alternate fixation member. Shown is the bone engaging member 304 having a head engagement portion 306 which is generally located below the shelf member 302. The head engagement portion 306 is shown as a female Morse taper 316. The annular engagement flange 318 is disposed on the upper surface 320 about the aperture 328 of the shelf member 302 Defined in the bottom of the Female Morse taper 316 is the drive mechanism 312.

Figure 38:
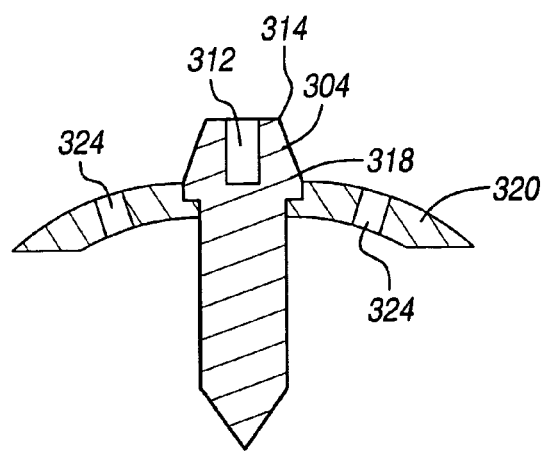
FIG. 38 represents a fixation member having a concave shelf member.

FIG. 38 shows the bone engagement member 304 with annular engagement flange 318. The annular engagement flange 318 is positioned on the convex upper surface 320 of the annular shelf member 302. The shelf member 302 defines an annular engagement groove adjacent the aperture which annularly supports the male Morse taper of the bone engaging member 304.

FIG. 39a-39b represents the implantation of a fixation member. Once the surface of the resected head 36 of the humerus 38 has been resected, the shelf member 302 positioned adjacent to the resected head 36. The bone engagement member 304 is inserted into the guide hole 90. It is envisioned that the bone engagement member 302 can be forced into the guide hole 90 to displace the bone material around the intramedullary canal.

Once the bone engagement member 302 has been inserted into the guide hole 90, the bone engagement member 302 is rotated until the annular engagement flange 318 engages the upper surface 320 of the annular shelf member 302. Optional screws 85 are disposed through the holes 324 to couple the base member 302 to the humerus 38. At this point, a surgeon may use any number of test head portions and/or adapter portions to determine the proper size needed to mate with the glenoid component. Once a proper head member size has been determined, the final head member 330 can be fixed to the head engagement portion 306 of the bone engaging member 302.

The description of the invention is merely exemplary embodiments in the present invention. One skilled in the art would readily recognize from such discussion and from accompanying drawings and claims that various changes, modifications, variations may be made therein without departing from the spirit and scope of the invention.

What is claimed is:

1. A set of surgical components for use in a joint arthroplasty to reconstruct a head of a joint, the set of surgical components comprising:
   a modular joint component implanted into the joint having a head portion and a neck portion to engage an articulating surface, said modular joint component including a head member having a first convex articulating surface and a second fixation surface, said first articulating surface in rotational and transitional contact with said modular joint component and said second fixation surface having a first coupling mechanism secured to a fixation component, said fixation component having a second coupling mechanism extending from a first medial surface and fixably secured to said first coupling mechanism of said head member and a second generally spherical surface defined about a central axis of said fixation component, said fixation component having a depending fixation peg completely surrounding said central axis over its length, said fixation peg secured to the head of the joint within only one of said head portion and said neck portion and terminating within one of the head and neck of the joint, said fixation peg defining a central fastener accepting aperture formed along the central axis; and
   a spherical reamer operable to prepare a surface of the joint.

2. The set of surgical components as defined in claim 1 wherein said spherical reamer is a concave spherical reamer.

3. The set of surgical components as defined in claim 1 wherein said second surface of said fixation component has a spherical convex shape.

4. The set of surgical components as defined in claim 1 further comprising a coupling member operable to be removably secured between said head member and said fixation component.

5. The set of surgical components as defined in claim 1 wherein said fixation component defines a plurality of holes passing through said first medial surface and said second generally spherical surface.

6. The set of surgical components as defined in claim 5 further comprising a plurality of fasteners disposed within said plurality of holes.

7. The set of surgical components as defined in claim 6 wherein said plurality of fasteners are bone screws.

8. A set of surgical components for use in a joint arthroplasty to reconstruct a head of a joint, the set of surgical components comprising:
   a modular joint component implanted into the joint having a head portion and a neck portion to engage an articulating surface, said modular joint component including a head member having a first convex articulating surface and a second fixation surface, said first articulating surface in rotational and transitional contact with said modular joint component and said second fixation surface having a first coupling mechanism secured to a fixation component, said fixation component having a second coupling mechanism extending from a first medial surface and fixably secured to said first coupling mechanism of said head member and a second generally spherical surface defined about a central axis of said fixation component, said fixation component having a depending fixation peg completely surrounding said central axis over its length, said fixation peg secured to the head of the joint within only one of said head portion and said neck portion and terminating within one of the head and neck of the joint, said fixation peg defining a central fastener accepting aperture; and
   a concave spherical reamer operable to prepare a surface of the joint,
   wherein said second surface of said fixation component has a spherical concave shape.

9. A set of surgical components for use in a joint arthroplasty to reconstruct a joint having a head and a neck, the set of surgical components comprising:
   a spherical reamer configured to prepare a surface of the head of the joint; and
   a modular prosthetic implanted into the prepared joint to engage an opposing articulating surface, said modular prosthetic further comprising:
   a head member having a first convex articulating surface in rotational and transitional contact with said opposing articulating surface and a second fixation surface having a first portion of a mating mechanism extending from said second fixation surface; and
   a fixation component fixably secured to the head of the joint having a second portion of said mating mechanism extending from a first medial surface and a second generally spherical surface defined about a central axis of said fixation component and including a depending fixation peg having a length, wherein said length of said depending fixation peg is coaxial with said central axis and is located completely within the head of the joint, said depending fixation peg defining a fastener accepting aperture formed along the central axis.

10. The set of surgical components as defined in claim 9 wherein said spherical reamer is a convex spherical reamer.

11. The set of surgical components as defined in claim 10 wherein said second spherical surface of said fixation component has a spherical convex shape.

12. The set of surgical components as defined in claim 9 wherein said spherical reamer is a concave spherical reamer.

13. The set of surgical components as defined in claim 12 wherein said second spherical surface of said fixation component has a spherical concave shape.

14. The set of surgical components as defined in claim 9 further comprising a coupling member operable to be removably secured between said head member and said fixation component.

15. The set of surgical components as defined in claim 14 wherein said coupling member comprises a third portion of said mating mechanism, wherein said first, second, and third portions removably secure said head member to said fixation component.

16. A modular joint component for use in a joint arthroplasty, the modular joint component adapted to be implanted into a joint having a head and a neck to engage an articulating surface of the joint, the modular joint component comprising:
   a head member having a first articulating surface and a second fixation surface opposite said first articulating surface, said first articulating surface operable to engage the articulating surface of the joint and said second fixation surface secured to a fixation component; and
   said fixation component having a first surface secured to said second fixation surface of said head member and a second spherical surface which is generally opposite the first surface, said second spherical surface having a centrally disposed fixation member disposed about a central axis defined through the fixation component secured directly to bone and only within and terminating within one of the head or the head and neck of the joint, said fixation member defining a bone screw accepting aperture formed so as to extend along the central axis.

17. The set of surgical components as defined in claim 9 further comprising a glenoid prosthetic configured to mate with said head member, said glenoid prosthetic including said opposing articulating surface.

18. The modular joint component as defined in claim 16 wherein said fixation component first surface comprises a Morse taper.

19. The modular joint component as defined in claim 18 wherein the Morse taper is a male Morse taper.

20. The modular joint component as defined in claim 18 wherein the Morse taper is a female Morse taper.

21. The modular joint component as defined in claim 18 wherein the Morse taper defines a portion of the bone screw accepting aperture.

22. The modular joint component as defined in claim 19 wherein said first surface of said fixation component is at least one of a generally flat shape and a generally spherical shape.

23. The modular joint component as defined in claim 16 wherein said second surface of said fixation component has a spherical convex shape.

24. The modular joint component as defined in claim 16 wherein said first surface of said fixation component is at least one of a generally flat shape and a generally spherical shape.

25. The modular joint component of claim 16 wherein said fixation component has a generally planar shape.

26. A modular joint component for use in a joint arthroplasty, the modular joint component adapted to be implanted into a joint having a head and a neck to engage an articulating surface of the joint, the modular joint component comprising:
   a head member having a first articulating surface and a second fixation surface opposite said first articulating surface, said first articulating surface operable to engage the articulating surface of the joint and said second fixation surface secured to a fixation component; and said fixation component having a first surface secured to said second fixation surface of said head member and a second spherical surface which is generally opposite the first surface, said second spherical surface having a centrally disposed fixation member secured directly to bone and only within and terminating within one of the head or the head and neck of the joint, said fixation member defining a bone screw accepting aperture, wherein said second spherical surface of said fixation component has a spherical concave shape.

* * * * *

UNITED STATES PATENT AND TRADEMARK OFFICE
CERTIFICATE OF CORRECTION

Page 1 of 2

PATENT NO.         : 8,317,871 B2
APPLICATION NO.    : 10/930044
DATED              : November 27, 2012
INVENTOR(S)        : Kevin T. Stone et al.

It is certified that error appears in the above-identified patent and that said Letters Patent is hereby corrected as shown below:

In the Specifications

Column 3,
Line 44, after "member" insert --;--

Column 3,
Line 57, replace "FIG. 39a-39c represents" with --FIGS. 39a-39c represent--

Column 4,
Line 49, after "not" delete "to"

Column 8,
Line 33, after "of" delete "an"

Column 8,
Line 42, after "of" delete "a"

Column 8,
Line 45, replace "284a and 248b" with --284a and 284b--

Column 8,
Line 45, replace "fully though" with --fully through--

Column 8,
Line 56, after "screw" insert --is--

Column 8,
Line 58, replace "a articulating" with --an articulating--

Signed and Sealed this
Eleventh Day of March, 2014

Michelle K. Lee
*Deputy Director of the United States Patent and Trademark Office*

Column 8,
Line 60, replace "show" with --shown--

Column 8,
Line 62, replace "FIG. 1-14" with --FIGS. 1-14--

Column 8,
Line 64, replace "allow" with --allows--

Column 9,
Line 5, replace "represents a perspective" with --represent perspective--

Column 9,
Lines 36-37, after "positioned" insert --on--

Column 9,
Line 49, replace "Female" with --female--

Column 9,
Line 55, replace "show" with --shown--

Column 9,
Line 56, replace "a annular" with --an annular--

Column 9,
Line 65, after "302" insert --.--

Column 9,
Line 66, replace "Female" with --female--

Column 10,
Line 8, replace "FIG. 39a-39b" with --FIGS. 39a-39b--

Column 10,
Line 10, after "302" insert --is--